United States Patent [19]

Kupper

[11] Patent Number: 4,855,455
[45] Date of Patent: Aug. 8, 1989

[54] PREPARATION OF AMINO ACID DERIVATIVES

[75] Inventor: Robert J. Kupper, Mt. Airy, Md.
[73] Assignee: W. R. Grace & Co.-Conn., New York, N.Y.
[21] Appl. No.: 146,861
[22] Filed: Jan. 22, 1988
[51] Int. Cl.$^4$ .................. C07C 102/06; C07C 117/04; C07D 309/14; C07D 335/02
[52] U.S. Cl. ..................................... 549/88; 564/136; 564/137; 549/9; 549/28; 549/68; 549/346; 549/424; 549/480; 549/510; 552/12
[58] Field of Search ............... 260/349; 564/136, 137; 549/9, 28, 68, 88, 346, 424, 480, 510

[56] References Cited

U.S. PATENT DOCUMENTS 4,411,925 10/1983 Brennan et al. ..................... 426/548
4,517,379 5/1985 Brennan et al. ..................... 564/193

FOREIGN PATENT DOCUMENTS 54-157585 12/1979 Japan .
57-165357 2/1981 Japan .

OTHER PUBLICATIONS

Streitwieser and Heathcock, *Introduction to Organic Chemistry* (1985), pp. 767–768.
Tamura et al, Chem. Abstracts 93(5), 1980, Abst. No. 46731n.
Bertho et al, Chem. Abstracts 57(2) 1962, at 2326h.
Scholes et al, Chem. Abstracts 98(25) 1983, Abst. No. 216001 x.
Makino et al, Chem. Abstracts 105 (11), 1985, Abst. No. 97160z.
W. Frederick Huber, JACS 77, pp. 112–116 (1955).

*Primary Examiner*—Joseph Paul Brust
*Assistant Examiner*—Mary Sue Howard
*Attorney, Agent, or Firm*—Howard J. Troffkin

[57] ABSTRACT

A hydroxy-carboxylate ester is converted to an amino-acid-amide by replacement of the —OH group with —N$_3$, via, e.g., CH$_3$SO$_2$Cl and NaN$_3$; reacting with amine to convert the ester to amide; and hydrogenating —N$_3$ to —NH$_2$. The present process alleviates the conventional use of blocking-deblocking procedures.

19 Claims, No Drawings

PREPARATION OF AMINO ACID DERIVATIVES

FIELD OF THE INVENTION

The present invention relates to a novel synthesis of optically active amino-amides which are useful in the preparation of sweeteners and for other purposes. Certain compounds derived and utilized in the synthesis are believed novel.

BACKGROUND

W. R. Huber, J.A.C.S. 77, 112–116 (1955) discloses a method (p. 112) for making racemic mixtures of aminoacyl glycerides by treating an alpha-halogen ester with sodium azide to form an alpha-azido ester, which was then saponified to give the alpha-azido acid. This acid was then converted to the acid chloride with thionyl chloride, which was, in turn, reacted with glycerol, or a monoglyceride, or a diglyceride, to form a tri-, di-, or mono-alpha-azidoacyl glyceride. The formation of the glyceride was accomplished via a ketene intermediate and yielded a racemic mixture. The formal glyceride was hydrogenated to convert the azido group to an amino group. On p. 113, Col. 1, the paper states that an alpha-aminoacyl glyceride was treated with an alpha-azidoacryl chloride "to yield an alpha-azido-acylaminoacyl glyceride which, on hydrogenation, yielded the 'dipeptide-glyceride'." The relevant reactions are considered to be:

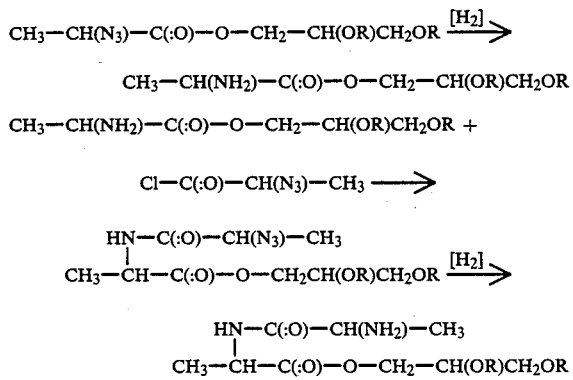

In the Huber paper R is identified as a long chain fatty residue, such as laurin, palmitin, stearin, etc. Note that the ester moiety (glyceryl) is retained intact and is not converted to amide. My ester group, on the other hand, reacts with and is replaced by amine to form an amide group.

In the Huber synthesis, the ester moiety (glyceryl) is retained in tact and is not converted to an amide, as presently achieved. Further, Huber's synthesis provides a product which is a racemic mixture and is not capable of achieving an optically active product nor one which is substantially free of one enantiomer as is possible by the present invention.

SUMMARY OF THE INVENTION

The present invention provides a synthesis for forming optically active amino-amides in four sequential steps. The present synthesis utilizes readily available hydroxy carboxylic acid esters and provides substantially one enantiomer of the resultant amino-amide product.

DETAILED DESCRIPTION OF THE INVENTION

A hydroxy-carboxylate ester is converted to an amino-amide in four sequential steps:

In Step I the hydroxyl group is replaced by a group capable of reacting with an azide salt. This group is called herein an azido-coupler, and it will be defined and described in detail later in this specification. The reaction in this first Step I is (using methane sulfonyl chloride as the azido-coupler exemplar with triethylamine as the base to neutralize by-product HCl):

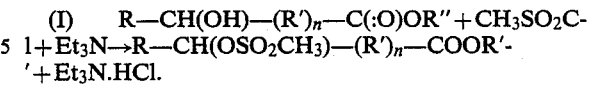

The thus-modified ester is then reacted with an azide salt; this completes the replacement of —OH with —N$_3$. Thus:

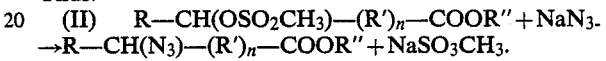

The azido-ester of reaction (II) is treated with an amine to yield the corresponding amide according to the following reaction:

The azido-amide of reaction (III) is now hydrogenated to form the amino-amide according to reaction (IV) below:

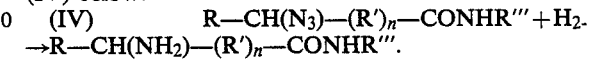

In each of the above equations:
R is H or alkyl of 1–18 carbons;
R' is —CH$_2$—;
n is 0–8;
R" is alkyl of 1–18 carbons; and
R''' is a monovalent organic radical.

It is believed that prior to the present invention, there was no practical way to proceed from a hydroxy-carboxylic ester to an amino-amide nor was there any practical way to proceed from an amino carboxylic ester to an amino-amide without first blocking the amino group. The contribution to this art by the present invention is to provide a synthesis for converting a hydroxy-carboxylate to an amino-amide in a series of simple steps, using generally inexpensive reactants and reagents. In the present process the hydroxyl group of the hydroxyl carboxylic ester is converted to a primary amino group, and the carboxylate group is converted to an amide group, all without the use of a blocking agent.

The present invention is particularly useful in the preparation of the D-alanine-amides. In the past the only practical way to prepare the D-alanine-amides required starting with D-alanine, blocking the amino group, esterifying, reacting with an amine to convert the ester group to an amide group, and finally deblocking to form the desired D-alanine-amide. This blocking-deblocking process is described in U.S. Pat. No. 4,411,925, Example 16, where N-t-butoxy-carbonyl-D-alanine is reacted with 3-amino-2,2,4,4-tetra-methylthietane to form the corresponding t-Boc-D-alanine-amide, which was then hydrolyzed to form the free alpha-amino-amide in 43% yield.

D-alanine is relatively expensive. The present process has unexpectedly been found to achieve the same end product (D-alanine-amide) starting from lactic acid ester, which is relatively cheap. The D-enantiomer is formed in reaction II and no other transformation occurs during subsequent reactions which change the integrety of the optical center.

The Hydroxy Carboxylic Esters

The process is applicable to the esters of hydroxy carboxylic acids generally. These acids include:

Alpha-hydroxy acids, e.g., glycolic, lactic, alpha-hydroxy butyric, alpha-hydroxy-n- and -iso-valeric acids; etc.;

Beta-hydroxy acids, e.g., beta-hydroxy propionic acid, beta-hydroxybutyric, beta-hydroxy valeric acid; etc.;

Gamma-hydroxy acids, e.g., gamma-hydroxy butyric acid, gamma-hydroxy valeric acid, etc.;

Other hydroxy carboxylic acids which are useful include delta-hydroxy valeric acid, epsilon-hydroxy caproic acid, and the like.

Azido-Coupler

In Step I of the 4-step invention process, the hydroxyl group is replaced by a group capable of reacting with an azide salt (i.e., an azide-reactable group). This can be accomplished with what is herein called an "azido-coupler." There are at least two basic types of azido-coupler. One type (preferred) reacts with and replaces the H atom of the —OH group. Another type replaces the whole —OH group.

The first type includes, by way of example, methane sulfonylchloride, toluene sulfonylchloride, benzyl sulfonylchloride, and the like. The class reaction (with methane sulfonylchloride as exemplar) is given above. The resulting methane sulfonyl derivative reacts readily with the azide salt in Step II, as indicated above.

The second type of azido-coupler includes, by way of example, $PX_3$ or $PX_5$ where X represents a halogen atom, preferably chlorine or bromine; and $SOCl_2$. The class reaction (with thionyl chloride as exemplar) is —CH(OH)—+SOCl$_2$→—CH(Cl)—+HCl+SO$_2$.

The chloro-compound reacts readily with the azide salt in Step II above.

The Azide Salt

The cheapest and easiest to use is sodium azide, $NaN_3$ although $KN_3$, $TlN_3$, and other azide salts may be used. As is well known, the azides are heat-sensitive, and care should be taken in their use.

The Amine

Substantially any primary or secondary amine is operable in the present invention process.

The following are useful:

Alkyl amines (linear or branched):

$H_xN(C_nH_{2n+1})_{3-x}$ where n=1 to 18 and x=1 or 2. Further, this group includes $H_2NR'''$, where $R'''$ is a branched member, as for example, a member selected from diiopropylcarbinyl, d-methyl-t-butylcarbinyl, d-ethyl-t-butylcarbinyl, di-t-butylcarbinyl, 2-methylthio-2,4-dimethylpentan-3-yl as well as the carbocyclic and heterocyclic groups described hereinbelow.

Cycloalkyl amines:

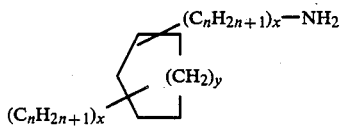

where n is independently 1–8; y is 0 or 1; and x is independently 0–4.

Aromatic amines (aralkyl, alkaryl, and the like):

where n = 1–4 and x = independently 0–5.

Carbo- and heterocyclic amines: This group includes $H_2NR'''$ where $R'''$ is a carbocyclic group such as fenchyl or

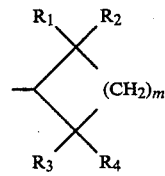

or a heterocyclic group, such as

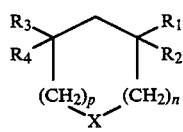

where at least one of $R_1$, $R_2$, $R_3$, $R_4$ is alkyl having from 1 to 4 carbon atoms and the remainder are hydrogen or alkyl having from 1 to 4 carbon atoms; X is O, S, SO, $SO_2$, C=O or CHOH; m is zero, 1, 2, 3, or 4; n and p are each zero, 1, 2, or 3, and the sum of n+p is not greater than 3; the sum of the carbon atoms in $R_1$, $R_2$, $R_3$, and $R_4$ is not greater than 6; and when both or $R_1$ and $R_2$ or $R_3$ and $R_4$ are alkyl they are methyl or ethyl.

A preferred amine of this group is 3-amino-2,2,4,4-tetramethylthietane.

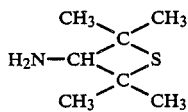

Amines of the above carbo- and hetero-cyclic groups are known. See U.S. Pat. No. 4,517,379, especially at Col. 12, lines 14 et seq. The contents of U.S. Pat. No. 4,517,379 in its entirety are herein incorporated by reference.

In summary, the amine can be an amino group attached to substantially any organic radical.

Hydrogenation

The hydrogenation reaction of step (IV) can be carried out using conventional hydrogenation conditions and catalysts. For example, the reaction can be carried out using hydrogen (low to moderate pressure) in the presence of a supported catalyst of Pd, Pt, Rh and the like or a Raney catalyst of Co, Ni, Fe and the like. It has been observed that the hydrogenation can be accomplished under mild conditions and even with the use of a Raney catalyst without the need of additional hydrogen being present, as illustrated by Example 3 hereinbelow. This was possible because Raney catalysts conventionally carry a substantial amount of adsorbed hydrogen, resulting from the activation process and because the hydrogen requirement in the Example was comparatively modest.

The following Examples are given for illustrative purposes only and are not meant to be a limitation on the present invention as defined by the claims appended hereto. All parts are by weight unless otherwise stated.

EXAMPLE 1

An equal molar solution of (S)-ethyl lactate and triethylamine in dry methylene was treated with an equal molar amount of methane sulfonylchloride at 5°–10° C. After the addition was complete, the mixture was filtered to remove triethylamine hydrochloride. The filtrate was then washed with water, dried over $MgSO_4$, and concentrated to give a high yield of ethyl-(S)-2[(methylsulfonyl)oxy]propionate.

EXAMPLE 2

One mole of the compound made in Example 1 was added with vigorous stirring to a solution of 1.1 mole of sodium azide in 200 mL of water and 100 mL of methanol. The resulting mixture was stirred for 24 hours, extracted with methylene chloride, dried over $MgSO_4$ and concentrated in vacuo at 25° C. to give (R)-ethyl-2-azidopropionate in nearly quantitative yield.

EXAMPLE 3

A 14.3 g sample of (R)-ethyl-2-azidopropionate was taken up in 50 mL of isopropylamine and allowed to stand for 24 hours. After stripping excess amine, 14.8 g of pure N-isopropyl-2-azidopropionamide was obtained. The amide thus obtained, 3.12 g, was stirred with 5.0 g of Raney nickel catalyst in 40 mL of isopropanol until nitrogen evolution ceased. The solution was filtered and concentrated in vacuo at 40° C. to give 2.5 g of crude N-isopropyl-D-alanine amide.

EXAMPLE 4

$$CH_3CH(N_3)COOC_2H_5 \rightarrow CH_3CH(N_3)COOH$$

Into a 2 L beaker was placed 200 mL of methanol, 800 mL of water, and 425 g (2.97 moles) of the azido-ester of Example 2. The resulting biphasic system was then saponified with 6N sodium hydroxide at 0°–7° C. pH=12.2. After complete saponification the pH was lowered to 8.0 and the solution was extracted with 2×500 mL of $CH_2Cl_2$. The methanol was then removed in vacuo and the aqueous phase acidified to pH=1.0 with concentrated HCl. The resulting solution was then extracted with 3×300 mL $CH_2Cl_2$, washed with saturated brine, dried over $MgSO_4$, filtered, and concentrated in vacuo at 25° C. to give 323.25 g (95% yield) of (R)-2-azido propionic acid as a pale yellow oil.

EXAMPLE 5

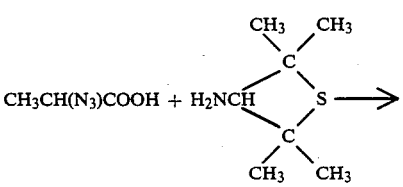

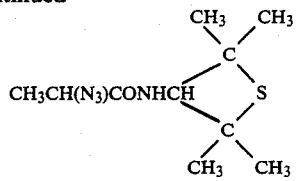

Into a sealed flask was placed 1.15 g of (R)-2-azido-propionic acid, 25 mL of dry tetrahydrofurane and 1.1 g of triethylamine. The resulting solution was chilled to −10° to −7° C. and treated with 1.36 g of isobutyl-chloroformate. After 5 minutes a solution of 1.45 g of 3-amino-2,2,4,4-tetramethylthietane in 10 mL of tetrahydrofurane was added. The solution was allowed to warm to room temperature and was stirred an additional 6 hours. The solution was then stripped of solvent, taken up in dichloromethane, and washed with 3×25 mL of 1N hydrochloric acid and 1×25 mL of saturated sodium bicarbonate solution. The organic phase was then dried over $MgSO_4$, filtered, and concentrated in vacuo at 40° C. to give 1.94 g of azido-amide.

EXAMPLE 6

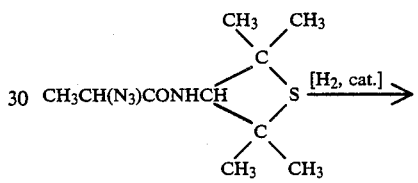

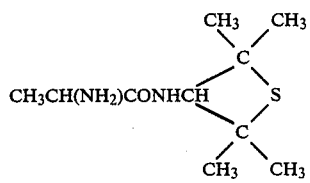

The azido-amide, 1.0 g, was dissolved in 25 mL of isopropyl alcohol and cooled to 0°–5° C. To this was added 2.5 g of Raney nickel catalyst. After the vigorous evolution of nitrogen ceased (4 to 10 minutes) the reaction mass was filtered from the catalyst and concentrated in vacuo at 40° C. to give a green oil. This material was taken up in ether, washed with a pH=9.0 solution of ethylene diamine tetraacetic acid, dried over $Na_2SO_4$ and concentrated to give 795 mg of a colorless oil homogeneous on silica gel TLC with consistent spectra properties.

What is claimed:

1. A process of forming an azido-amide comprising:
   (A) reacting the hydroxyl group of a hydroxy-carboxylic ester of the formula:

$$R-CH(OH)-(R')_n-COOR'' \quad (I)$$

with an azido-coupler to replace the hydroxyl group or the hydrogen atom of the hydroxyl group with an azide reactable group;
   then (B) reacting the product of (A) above with an inorganic azide salt to form an azido-ester of the formula:

$$R-CH(N_3)-(R')_n-COOR'' \quad (II)$$

and then (C) reacting the azido-ester product of (B) above with a primary or secondary amine selected from:
(a) a linear or branched alkylamine of the formula $H_xN(C_nH_{2n+1})_{3-x}$ wherein n is 1 to 18 and x is 1 or 2; or
(b) a cycloalkyl amine of the formula:

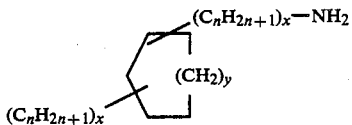

where n is independently 1–8;
y is 0 or 1; and x is independently 0–4

(c) an aromatic amine of the formula:

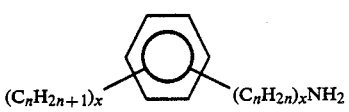

where n = 1–4 and x = independently 0–5

(d) carbo cyclic amines

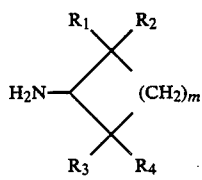

wherein at least one $R_1$, $R_2$, $R_3$, and $R_4$ is a $C_1$–$C_4$ alkyl and the remainder are hydrogen or a $C_1$–$C_4$ alkyl and m is an interger of 1 to 4;
and (e) a heterocyclic amine of the formula

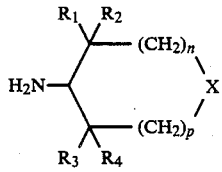

wherein x represents O, SO, $SO_2$, C=O, or CHOH; n and p each represent o, 1, 2 or 3 and the sum of n+p is not greater than 3; and at least one $R_1$, $R_2$, $R_3$ and $R_4$ is a $C_1$–$C_4$ alkyl and the remainder are hydrogen or $C_1$–$C_4$ alkyl and the sum of the carbon atoms of $R_1$, $R_2$, $R_3$ and $R_4$ is not greater than 6; to form an azido-amide of the formula $$R-CH(N_3)-(R')_n-CONR''' \qquad (III)$$

wherein in said formulas I, II and III above the symbols R represents H or a $C_1$–$C_{18}$ alkyl, R' represents —$CH_2$—, n represents an integer of 0 to 8, R" represents a $C_1$–$C_{18}$ alkyl, and R''' represents a monovalent organic residual radical of said amine defined above.

2. The process of claim 1 wherein the azido-amide of III is contacted with hydrogen at low to moderate pressures in the presence of a hydrogenation catalyst to form an amino-amide of the formula $$R-CH(NH_2)-(R')_n-CONHR''' \qquad (IV)$$

wherein the symbols R, R' and R''' are the same as for formulas I, II and III.

3. Process according to claim 1 wherein the hydroxy-carboxylic ester is (S)-ethyl lactate; the azido-coupler is methane sulfonylchloride; and the azide salt is sodium azide.

4. Process according to claim 2 wherein the hydroxy-carboxylic ester is (S)-ethyl lactate; the azido-coupler is methane sulfonylchloride; and the azide salt is sodium azide.

5. Process of making N-isopropyl-D-alanine amide according to claim 2 wherein the hydroxy-carboxylic ester is (S)-ethyl lactate; the azido-coupler is methane sulfonylchloride; the azide salt is alkali metal azide; and the amine is N-isopropylamine.

6. Process according to claim 5 wherein the hydroxy-carboxylic ester is (S)-ethyl lactate; the azido-coupler is methane sulfonylchloride; and the azide salt is sodium azide.

7. Process according to claim 2 wherein the amine used to form the azido-amide is selected from fenchyl, diisopropyl carbinyl, d-methyl-t-butyl carbinyl, d-ethyl-t-butyl carbinyl, di-t-butyl carbinyl and 2-methylthio-2,4-dimethyl pentan-3-yl.

8. Process according to claim 1 wherein the amine is selected from the linear or branched alkylamines (a).

9. Process according to claim 1 wherein the amine is selected from the cycloalkyl amine (b).

10. Process according to claim 1 wherein the amine is selected from the aromatic amines (c).

11. Process according to claim 1 wherein the amine is selected from the carbocylic amines (d).

12. Process according to claim 1 wherein the amine is selected from the heterocylic amines (e).

13. Process according to claim 1 wherein the amine is a member of the group consisting of isopropylamine or 3-amino-2,2,4,4-tetramethylthietane.

14. An azido-amide of the structure $$R-CH(N_3)-(R')_n-CONHR'''$$

where R is H or alkyl of 1–18 carbons; R' represents —$CH_2$—, n represents an integer of 0 to 8; and R''' is a straight or branched alkyl group represented by $$(C_nH_{2n+1})-$$

wherein n is an integer of 1 to 18, a cycloalkyl group represented by

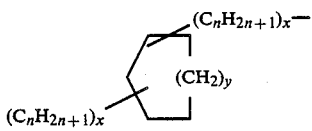

wherein n is an integer of 1 to 8, y is an integer of 0 or 1 and x is independently an integer of 0 to 4, a carbocyclic group represented by

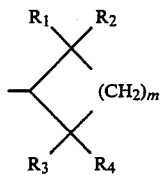

wherein at least one $R_1$, $R_2$, $R_3$ and $R_4$ is $C_1$–$C_4$ alkyl with the remainder being hydrogen or $C_1$–$C_4$ alkyl and m is an integer of 1 to 4, or an alkyl substituted heterocyclic group represented by

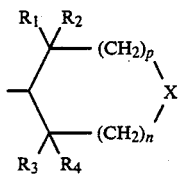

wherein at least one of $R_1$, $R_2$, $R_3$, and $R_4$ is $C_1$–$C_4$ alkyl with the remainder being hydrogen or $C_1$–$C_4$ alkyl, and the sum of the carbon atoms of $R_1$, $R_2$, $R_3$, and $R_4$ is not greater than 6; x is O, S, SO, $SO_2$, C=O, or CHOH; n and p each represent 0, 1, 2 or 3 and the sum of n+p is not greater than 3.

15. The azido-amide of claim 14 wherein the R''' is a straight or branched alkyl group represented by $(C_nH_{2n+1})$— wherein n is an integer of 1 to 18.

16. The azido-amide of claim 14 wherein the R''' represents

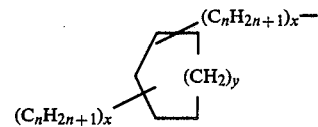

wherein n is an integer of 1 to 8, y is an integer of 0 or 1 and x is independently an integer of 0 to 4.

17. The azido-amide of claim 14 wherein the R''' represents a carbocyclic group of the structure

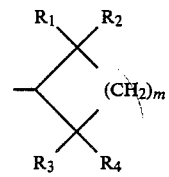

wherein at least one $R_1$ $R_2$, $R_3$ and $R_4$ is a $C_1$–$C_4$ alkyl with the remainder being hydrogen or $C_1$–$C_4$ alkyl and m is an integer of 1 to 4.

18. The azido-amide of claim 14 wherein the R''' represents a heterocyclic group of the structure

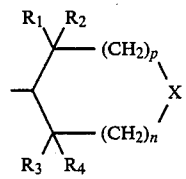

wherein at least an $R_1$ $R_2$, $R_3$ and $R_4$ is a $C_1$–$C_4$ alkyl with the remainder being hydrogen or $C_1$–$C_4$ alkyl, X is O, S, SO, $SO_2$, C=O or CHOH and p and n are each integers of 0 to 3 and the sum of n+p is not greater than 3.

19. The azido-amide according to claim 14 where R''' is a member of the group consisting of isopropyl, and tetramethylthietanyl.

* * * * *

UNITED STATES PATENT AND TRADEMARK OFFICE
CERTIFICATE OF CORRECTION

PATENT NO. : 4,855,455

DATED : August 8, 1989

INVENTOR(S) : Robert J. Kupper

It is certified that error appears in the above-identified patent and that said Letters Patent is hereby corrected as shown below:

In Claim 1, subpara. (e) at the first line of text after the formula:

delete "wherein x represents O, SO, SO, $SO_2$"
and insert --wherein x represents O, S, SO, $SO_2$--

Signed and Sealed this

Fifth Day of June, 1990

Attest:

HARRY F. MANBECK, JR.

*Attesting Officer*     *Commissioner of Patents and Trademarks*